US008536213B2

(12) United States Patent
Riggs-Sauthier et al.

(10) Patent No.: US 8,536,213 B2
(45) Date of Patent: Sep. 17, 2013

(54) OLIGOMER-DANTROLENE CONJUGATES AND RELATED COMPOUNDS

(75) Inventors: Jennifer Riggs-Sauthier, Huntsville, AL (US); Wen Zhang, Madison, AL (US)

(73) Assignee: Nektar Therapeutics, San Francisco, CA (US)

(*) Notice: Subject to any disclaimer, the term of this patent is extended or adjusted under 35 U.S.C. 154(b) by 426 days.

(21) Appl. No.: 12/742,432
(22) PCT Filed: Nov. 14, 2008
(86) PCT No.: PCT/US2008/012806
§ 371 (c)(1),
(2), (4) Date: Jul. 29, 2010
(87) PCT Pub. No.: WO2009/067175
PCT Pub. Date: May 28, 2009

(65) Prior Publication Data
US 2010/0317705 A1    Dec. 16, 2010

Related U.S. Application Data

(60) Provisional application No. 61/003,380, filed on Nov. 16, 2007, provisional application No. 61/069,125, filed on Mar. 12, 2008.

(51) Int. Cl.
*A01N 43/50* (2006.01)
*A61K 31/415* (2006.01)
*C07D 211/72* (2006.01)
*C07D 211/84* (2006.01)
*C07D 213/56* (2006.01)
*C07D 201/16* (2006.01)

(52) U.S. Cl.
USPC ............................. 514/390; 548/316.1; 540/1

(58) Field of Classification Search
USPC ........................... 514/390; 548/316.1; 540/1
See application file for complete search history.

(56) References Cited

U.S. PATENT DOCUMENTS

| 3,415,821 | A | 12/1968 | Davis et al. |
| 5,672,662 | A | 9/1997 | Harris et al. |
| 2002/0123609 | A1 | 9/2002 | Frechet et al. |
| 2005/0136031 | A1 | 6/2005 | Bentley et al. |
| 2009/0093531 | A1 | 4/2009 | Malkawi |

FOREIGN PATENT DOCUMENTS

| WO | WO 02/098949 | | 12/2002 |
| WO | WO 03/037385 | A1 | 5/2003 |
| WO | WO 2005/013919 | | 2/2005 |
| WO | WO 2005/058367 | | 6/2005 |
| WO | WO 2008/112286 | | 9/2008 |

OTHER PUBLICATIONS

Chen, et al., "Synthesis and Properties of ABA Amphiphiles," J. Org. Chem., vol. 64, pp. 6870-6873, (1999).
Crumb, Jr., et al., "Comparison of Ito in young and adult human atrial myocytes: evidence for developmental changes," Amer. Physio. Soc., vol. 268, pp. H1335-H1342, (1995).
Eknoian, et al., "New Biocidal N-Halamine-PEG Polymers," J. of Bioact. & Comp. Poly., vol. 13, No. 2, pp. 135-145, (1998).
Ertl, et al., "Fast Calculation of Molecular Polar Surface Area as a Sum of Fragment-Based Contributions and Its Applications to the Prediction of Drug Transport Properties," J. Med. Chem., vol. 43, pp. 3714-3717, (2000).
Greenwald, et al., "Poly(ethylene glycol) Conjugated Drugs and Prodrugs: A Comprehensive Review," Crit. Rev. in Therapeu. Drug Carr. Sys., vol. 17, No. 2, pp. 101-161, (2000).
Kelder, et al., "Polar Molecular Surface as a Dominating Determinant for Oral Absorption and Brain Penetration of Drugs," Pharmaceu. Res., vol. 16, No. 10, pp. 1514-1519, (1999).
Krause, et al., "Dantrolene—A review of Its pharmacology, therapeutic use and new developments," Anaest. Acad., vol. 59, pp. 364-373, (2004).
Pasut, et al., "Protein, peptide and non-peptide drug PEGylation for therapeutic application," Exp. Opin., vol. 14, No. 6, pp. 859-894, (2004).
PCT International Search Report corresponding to PCT Application No. PCT/US2008/012806 date of mailling Jun. 15, 2009.
PCT International Preliminary Report on Patentability corresponding to PCT Application No. PCT/US2008/012806 date of mailing May 27, 2010.
Enzon Pharmaceuticals, Macromolecular Engineering Technologies, pp. 1-14, (2004).
Nektar™—Transforming Therapeutics, Nektar Molecule Engineering: Polyethylene Glycol and Derivatives for Advanced PEGylation, pp. 1-20, Catalog—2003, (Jul. 2003).
Nektar™—Transforming Therapeutics, Nektar Advanced PEGylation: Polyethylene Glycol and Derivatives for Advanced PEGylation, pp. 1-24, Catalog—2004, (Jul. 2004).
Nektar™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid and Drug Delivery Materials for Pharmaceuticals", pp. 1-46, Catalogue 2003—1st, (Jan. 2003).
NOF Corporation, "PEG Derivatives, Phospholipid and Drug Delivery Materials for Pharmaceuticals", pp. 1-50, Catalogue 2003—2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; BIOTINS, (Apr. 2004).
Polypure, Products; PEG amines; PEG acids and amino acids; PEG thiols and disulfides; BIOTINS, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).

*Primary Examiner* — Sreeni Padmanabhan
*Assistant Examiner* — Uma Ramachandran
(74) *Attorney, Agent, or Firm* — Mark A. Wilson

(57) ABSTRACT

The invention relates to (among other things) oligomer-dantrolene conjugates and related compounds. A conjugate of the invention, when administered by any of a number of administration routes, exhibits advantages over previously administered compounds.

12 Claims, 2 Drawing Sheets

OLIGOMER-DANTROLENE CONJUGATES AND RELATED COMPOUNDS

CROSS REFERENCE TO RELATED APPLICATIONS

This application is a 35 U.S.C. §371 application of International Application No. PCT/US2008/012806, filed Nov. 14, 2008, designating the United States, which claims the benefit of priority under 35 U.S.C. §119(e) to U.S. Provisional Patent Application Ser. No. 61/003,380, filed Nov. 16, 2007, and U.S. Provisional Patent Application Ser. No. 61/069,125, filed Mar. 12, 2008, all of which are incorporated herein by reference in their entireties.

FIELD OF THE INVENTION

This invention comprises (among other things) conjugates of a dantrolene moiety that possess certain advantages over the dantrolene moiety in unconjugated form. The conjugates (also referred to as "inventive compounds" and "compounds of the invention") described herein relate to and/or have application(s) in (among others) the fields of drug discovery, pharmacotherapy, physiology, organic chemistry and polymer chemistry.

BACKGROUND OF THE INVENTION

Dantrolene is indicated for the control of muscle spasticity and is commonly used as a muscle relaxant. In addition, dantrolene can be used in the treatment of patients suffering from hypermetabolism, which often manifests as hyperthermia. Dantrolene represents an important and widely used tool in pharmacotherapy.

Although dantrolene moieties serve an important role in treating patients, their use is sometimes associated with (among other things) CNS side effects, including drowsiness and dizziness. Reduction of CNS side effects from dantrolene and related compounds would enhance their desirability as therapeutic drugs.

The present invention seeks to address these and other needs in the art.

SUMMARY OF THE INVENTION

In one or more embodiments of the invention, a compound is provided, the compound comprising a dantrolene moiety residue covalently attached via a stable or degradable linkage to a water-soluble, non-peptidic oligomer.

Exemplary compounds of the invention include those having the following structure:

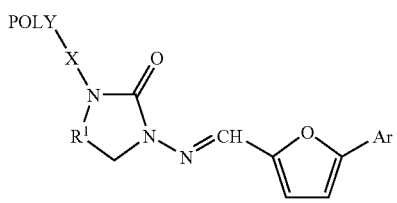
(Formula I-C)

wherein:
R$^1$ is carbonyl or methylene;
Ar is selected from the group consisting of furyl and phenyl each optionally substituted with one or two substituents selected from the group consisting of nitro, cyano, amino, chloro, bromo, acetyl, carboxy, methyl and trifluoromethyl;
X is a spacer moiety; and
POLY is a water-soluble, non-peptidic oligomer.

Further exemplary compounds of the invention include those encompassed by the following structure:

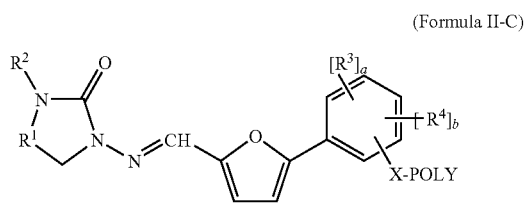
(Formula II-C)

wherein:
R$^1$ is carbonyl or methylene;
R$^2$ is a member of the group consisting of hydrogen, hydroxyethyl, alkyl, and 4-pyridylethyl;
(a) is either zero or one;
(b) is either zero or one;
R$^3$, when present, is selected from the group consisted of nitro, cyano, amino, chloro, bromo, acetyl, carboxy, methyl and trifluoromethyl;
R$^4$, when present, is selected from the group consisting of nitro, cyano, amino, chloro, bromo, acetyl, carboxy, methyl and trifluoromethyl;
X is a spacer moiety; and
POLY is a water-soluble, non-peptidic oligomer.

The "dantrolene moiety residue" is a compound having a structure of a dantrolene moiety that is altered by the presence of one or more bonds, which bonds serve to attach (either directly or indirectly) one or more water-soluble, non-peptidic oligomers.

In this regard, any compound having dantrolene activity can be used as a dantrolene moiety. Exemplary dantrolene moieties have a structure encompassed by Formula I,

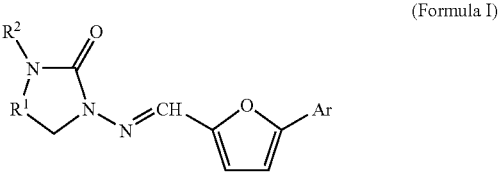
(Formula I)

wherein:
R$^1$ is carbonyl or methylene;
R$^2$ is a member of the group consisting of hydrogen, hydroxyethyl, alkyl, and 4-pyridylethyl; and
Ar is selected from the group consisting of furyl and phenyl each optionally substituted with one or two substituents selected from the group consisting of nitro, cyano, amino, chloro, bromo, acetyl, carboxy, methyl and trifluoromethyl.

Preferred dantrolene moieties of Formula I are encompassed by the following formula:

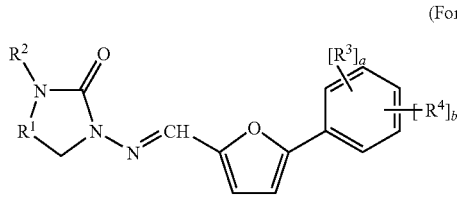

(Formula Ia)

wherein:
R¹ is carbonyl or methylene;
R² is a member of the group consisting of hydrogen, hydroxyethyl, alkyl, and 4-pyridylethyl;
(a) is either zero or one;
(b) is either zero or one;
R³, when present, is selected from the group consisted of nitro, cyano, amino, chloro, bromo, acetyl, carboxy, methyl and trifluoromethyl; and
R⁴, when present, is selected from the group consisting of nitro, cyano, amino, chloro, bromo, acetyl, carboxy, methyl and trifluoromethyl.

Further exemplary dantrolene moieties have a structure encompassed by Formula II,

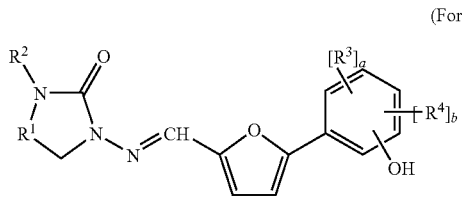

(Formula II)

wherein:
R¹ is carbonyl or methylene;
R² is a member of the group consisting of hydrogen, hydroxyethyl, alkyl, and 4-pyridylethyl;
(a) is either zero or one;
(b) is either zero or one;
R³, when present, is selected from the group consisted of nitro, cyano, amino, chloro, bromo, acetyl, carboxy, methyl and trifluoromethyl; and
R⁴, when present, is selected from the group consisting of nitro, cyano, amino, chloro, bromo, acetyl, carboxy, methyl and trifluoromethyl.

Preferred dantrolene moieties of Formula II are encompassed by the structure of Formula IIa, as shown below.

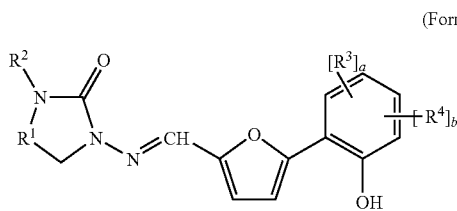

(Formula IIa)

wherein:
R¹ is carbonyl or methylene;
R² is a member of the group consisting of hydrogen, hydroxyethyl, alkyl, and 4-pyridylethyl;
(a) is either zero or one;
(b) is either zero or one;
R³, when present, is selected from the group consisted of nitro, cyano, amino, chloro, bromo, acetyl, carboxy, methyl and trifluoromethyl; and
R⁴, when present, is selected from the group consisting of nitro, cyano, amino, chloro, bromo, acetyl, carboxy, methyl and trifluoromethyl.

In one or more embodiments of the invention, a composition is provided, the composition comprising a compound comprising a dantrolene moiety residue covalently attached via a stable or degradable linkage to a water-soluble and non-peptidic oligomer, and optionally, a pharmaceutically acceptable excipient.

In one or more embodiments of the invention, a dosage form is provided, the dosage form comprising a compound comprising a dantrolene moiety residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a dantrolene moiety.

In one or more embodiments of the invention, a method is provided, the method comprising administering a compound comprising a dantrolene moiety residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

Figure 1:
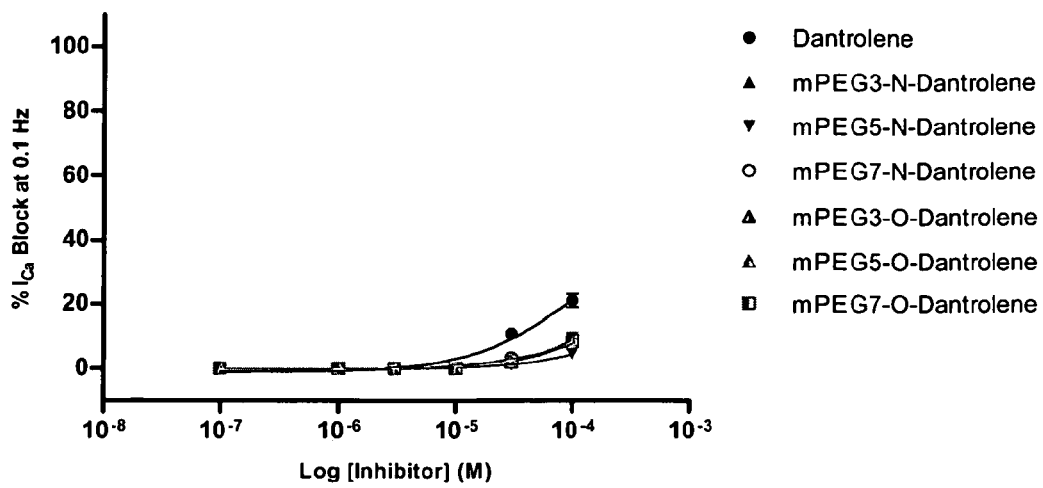
FIG. 1 shows the blocking effects of dantrolene and the compounds prepared in Examples 1 and 2 on calcium current at 0.1 Hz in isolated human atrial myocytes as further explained in Example 3. Data are mean±SEM.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the dantrolene moiety. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the dantrolene moiety. A composition comprised of bimodal conjugates may, however, include one or more nonconjugate substances such as solvents, reagents, excipients, and so forth.

A "dantrolene moiety" refers to an organic, inorganic, or organometallic compound having a molecular weight of less than about 1000 Daltons and having some degree of dantrolene activity. By using known assays, one of ordinary skill in the art will be able to determine whether any given compound has dantrolene activity. Among the activities of a dantrolene moiety, decreasing excitation-contraction coupling in skeletal muscle (via binding to the ryanodine receptor) and decreasing intracellular calcium concentrations via the same mechanism of dantrolene are exemplary.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to a component that may be included in the compositions of the invention causing no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a dantrolene moiety residue covalently attached via a stable or degradable linkage to a water-soluble, non-peptidic oligomer.

In one or more embodiments of the invention, a compound is provided, the compound comprising a dantrolene moiety residue covalently attached via a stable or degradable linkage to a water-soluble, non-peptidic oligomer. In this regard, any compound having dantrolene activity can be used as a dantrolene moiety. Exemplary dantrolene moieties have a structure encompassed by Formula I,

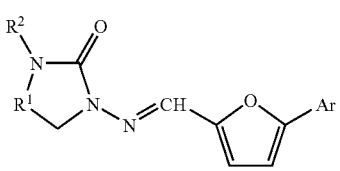

(Formula I)

wherein:
$R^1$ is carbonyl or methylene;
$R^2$ is a member of the group consisting of hydrogen, hydroxyethyl, alkyl, and 4-pyridylethyl;
Ar is selected from the group consisting of furyl and phenyl each optionally substituted with one or two substituents selected from the group consisting of nitro, cyano, amino, chloro, bromo, acetyl, carboxy, methyl and trifluoromethyl;

Preferred dantrolene moieties of Formula I are encompassed by the following formula:

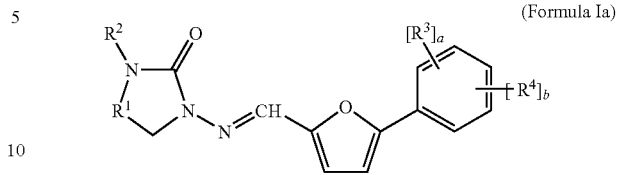

(Formula Ia)

wherein:
$R^1$ is carbonyl or methylene;
$R^2$ is a member of the group consisting of hydrogen, hydroxyethyl, alkyl, and 4-pyridylethyl;
  (a) is either zero or one;
  (b) is either zero or one;
$R^3$, when present, is selected from the group consisted of nitro, cyano, amino, chloro, bromo, acetyl, carboxy, methyl and trifluoromethyl; and
$R^4$, when present, is selected from the group consisting of nitro, cyano, amino, chloro, bromo, acetyl, carboxy, methyl and trifluoromethyl.

Further exemplary dantrolene moieties have a structure encompassed by
Formula II,

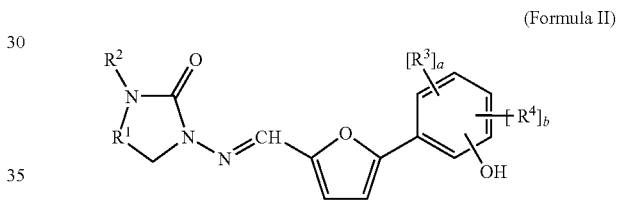

(Formula II)

wherein:
$R^1$ is carbonyl or methylene;
$R^2$ is a member of the group consisting of hydrogen, hydroxyethyl, alkyl, and 4-pyridylethyl; and
Ar is selected from the group consisting of furyl and phenyl each optionally substituted with one or two substituents selected from the group consisting of nitro, cyano, amino, chloro, bromo, acetyl, carboxy, methyl and trifluoromethyl.

Preferred dantrolene moieties of Formula II are encompassed by the structure of Formula IIa, as shown below.

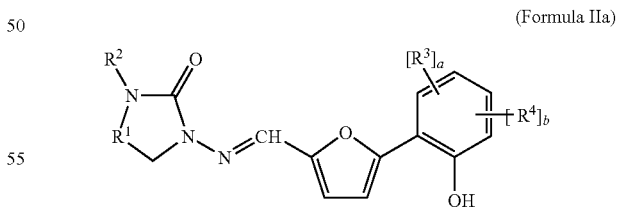

(Formula IIa)

wherein:
$R^1$ is carbonyl or methylene;
$R^2$ is a member of the group consisting of hydrogen, hydroxyethyl, alkyl, and 4-pyridylethyl;
  (a) is either zero or one;
  (b) is either zero or one;
$R^3$, when present, is selected from the group consisted of nitro, cyano, amino, chloro, bromo, acetyl, carboxy, methyl and trifluoromethyl; and R[4], when present, is selected from the group consisting of nitro, cyano, amino, chloro, bromo, acetyl, carboxy, methyl and trifluoromethyl.

Dantrolene moieties encompassed by Formulae I and Ia can be prepared according to known methods. See, for example, U.S. Pat. No. 3,415,821 for a description of one or more methods for preparing dantrolene moieties encompassed by or related to compounds having structures encompassed by Formula I. Dantrolene moieties encompassed by Formulae II and IIa can be prepared as described herein.

Exemplary compounds of the invention, then, are encompassed by the following formula:

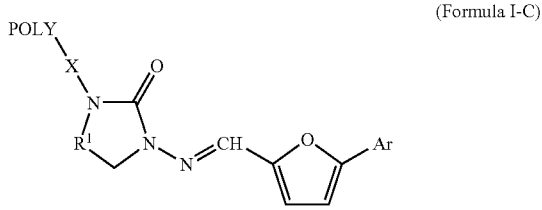

(Formula I-C)

wherein:

R[1] is carbonyl or methylene;

Ar is selected from the group consisting of furyl and phenyl each optionally substituted with one or two substituents selected from the group consisting of nitro, cyano, amino, chloro, bromo, acetyl, carboxy, methyl and trifluoromethyl;

X is a spacer moiety; and

POLY is a water-soluble, non-peptidic oligomer.

Preferred Formula I-C conjugates of the invention are encompassed by the following formula:

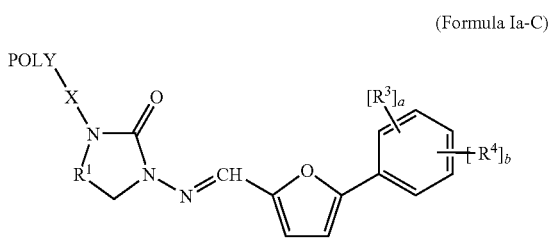

(Formula Ia-C)

wherein:

R[1] is carbonyl or methylene;

(a) is either zero or one;

(b) is either zero or one;

R[3], when present, is selected from the group consisted of nitro, cyano, amino, chloro, bromo, acetyl, carboxy, methyl and trifluoromethyl;

R[4], when present, is selected from the group consisting of nitro, cyano, amino, chloro, bromo, acetyl, carboxy, methyl and trifluoromethyl;

X is a spacer moiety; and

POLY is a water-soluble, non-peptidic oligomer.

Further exemplary compounds of the invention include those encompassed by the following structure:

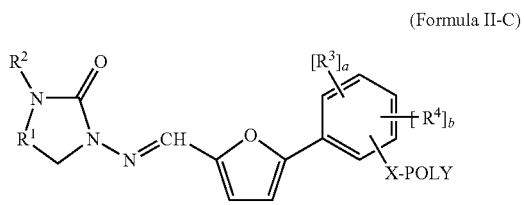

(Formula II-C)

wherein:

R[1] is carbonyl or methylene;

R[2] is a member of the group consisting of hydrogen, hydroxyethyl, alkyl, and 4-pyridylethyl;

(a) is either zero or one;

(b) is either zero or one;

R[3], when present, is selected from the group consisted of nitro, cyano, amino, chloro, bromo, acetyl, carboxy, methyl and trifluoromethyl;

R[4], when present, is selected from the group consisting of nitro, cyano, amino, chloro, bromo, acetyl, carboxy, methyl and trifluoromethyl;

X is a spacer moiety; and

POLY is a water-soluble, non-peptidic oligomer.

Preferred Formula II-C conjugates of the invention are encompassed by the following formula:

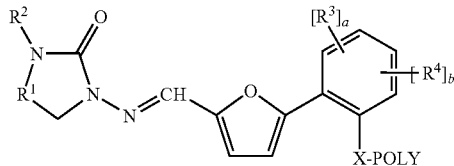

(Formula IIa-C)

wherein:

R[1] is carbonyl or methylene;

R[2] is a member of the group consisting of hydrogen, hydroxyethyl, alkyl, and 4-pyridylethyl;

(a) is either zero or one;

(b) is either zero or one;

R[3], when present, is selected from the group consisted of nitro, cyano, amino, chloro, bromo, acetyl, carboxy, methyl and trifluoromethyl;

R[4], when present, is selected from the group consisting of nitro, cyano, amino, chloro, bromo, acetyl, carboxy, methyl and trifluoromethyl;

X is a spacer moiety; and

POLY is a water-soluble, non-peptidic oligomer.

Use of oligomers (e.g., from a monodisperse or bimodal composition of oligomers, in contrast to relatively impure compositions) to form oligomer-containing compounds can advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability can be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug compound exhibits a blood-brain barrier crossing rate that is reduced as compared to the crossing rate of the small molecule drug not attached to the water-soluble, non-peptidic oligomer. Preferred exemplary reductions in blood-brain barrier crossing rates for the compounds described herein include reductions of: at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a compound of the invention is at least about 20%.

Assays for determining whether a given compound (regardless of whether the compound includes a water-soluble, non-peptidic oligomer or not) are known and/or can be prepared by one of ordinary skill in the art.

Each of these (and other) dantrolene moieties can be covalently attached (either directly or through one or more atoms) to a water-soluble and non-peptidic oligomer.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300, Daltons.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The dantrolene moiety for coupling to a water-soluble, non-peptidic oligomer possesses a free hydroxyl, carboxyl, thio, amino group, or the like (i.e., "handle") suitable for covalent attachment to the oligomer. In addition, the dantrolene moiety can be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble and non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3-(OCH_2CH_2)_n-$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the dantrolene moiety (in contrast to the step-wise addition of one or more monomers to effectively "grow" the oligomer onto the dantrolene), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8,1-9, 1-10, and so forth; 2-3, 2-4, 2-5, 2-6, 2-7, 2-8, 2-9, 2-10, and so forth; 3-4, 3-5, 3-6,3-7, 3-8, 3-9, 3-10, and so forth; 4-5, 4-6, 4-7, 4-8, 4-9, 4-10, and so forth; 5-6, 5-7, 5-8,5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble and non-peptidic oligomers can be prepared as described in Chen Y., Baker, G. L., *J. Org. Chem.*, 6870-6873 (1999), WO 02/098949, and U.S. Patent Application Publication 2005/0136031.

When present, the spacer moiety (through which the water-soluble and non-peptidic polymer is attached to the dantrolene moiety) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}-NH-(C=O)-NH-R'_{drug}$, is considered to have a chain length of 3 atoms ($-NH-C(O)-NH-$). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the dantrolene residue and the water-soluble, non-peptidic oligomer), $-C(O)O-$, $-OC(O)-$, $-CH_2-C(O)O-$, $-CH_2-OC(O)-$, $-C(O)O-CH_2-$, $-OC(O)-CH_2-$, $-O-$, $-NH-$, $-S-$, $C(O)-NH$, $NH-C(O)-NH$, $0-C(O)-NH$, $-C(S)-$, $-CH_2-$, $-CH_2-CH_2-$, $-CH_2-CH_2-CH_2-$, $-CH_2-CH_2-CH_2-CH_2-$, $-O-CH_2-$, $-CH_2-O-$, $-O-CH_2-CH_2-$, $-CH_2-O-CH_2-$, $-CH_2-CH_2-O-$, $-O-CH_2-CH_2-CH_2-$, $-CH_2-O-CH_2-CH_2-$, $-CH_2-CH_2-O-CH_2-$, $-O-CH_2-CH_2-CH_2-O-$, $-CH_2-CH_2-CH_2-O-$, $-O-CH_2-$ —CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—CH$_2$—CH$_2$—, —CH$_2$—CH$_2$—C(O)—,
—CH$_2$—CH$_2$—CH$_2$—C(O)—NH—CH$_2$—CH$_2$—NH—,
—CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the dantrolene moiety) with a corresponding functional group within the dantrolene moiety. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N═C═O) on a drug, or vice versa, forms a urea linkage (R—NH—(C═O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, all but one termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)-]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(═O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the dantrolene moiety may not have a functional group suited for conjugation. In this instance, it is possible to modify (or "functionalize") the "original" dantrolene moiety so that it does have a functional group suited for conjugation. For example, if the dantrolene moiety has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule dantrolene moiety bearing a carboxyl group wherein the carboxyl group-bearing small molecule dantrolene moiety is coupled to an amino-terminated oligomeric ethylene glycol, to provide a conjugate having an amide group covalently linking the small molecule dantrolene moiety to the oligomer. This can be performed, for example, by combining the carboxyl group-bearing small molecule dantrolene moiety with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule dantrolene moiety bearing a hydroxyl group wherein the hydroxyl group-bearing small molecule dantrolene moiety is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule dantrolene moiety bearing a hydroxyl group (such as, for example, the dantrolene moieties having structures encompassed within at least one of Formulae II and IIa) wherein the hydroxyl group-bearing small molecule dantrolene moiety is coupled to an oligomeric ethylene glycol bearing an haloformate group [e.g., $CH_3(OCH_2CH_2OC(O)$-halo, where halo is chloro, bromo, iodo] to result in an carbonate [—O—C(O)—O-] linked small molecule conjugate. This can be performed, for example, by combining a dantrolene moiety and an oligomeric ethylene glycol bearing an haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule dantrolene moiety bearing a ketone group by first reducing the ketone group to form the corresponding hydroxyl group. Thereafter, the small molecule dantrolene moiety now bearing a hydroxyl group can be coupled as described herein.

In still another instance, it is possible to prepare a conjugate of a small molecule dantrolene moiety bearing an amine group. In one approach, the amine group-bearing small molecule dantrolene moiety and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule dantrolene moiety and the carbonyl carbon of the aldehyde-bearing oligomer.

In another approach for preparing a conjugate of a small molecule dantrolene moiety bearing an amine group, a carboxylic acid-bearing oligomer and the amine group-bearing small molecule dantrolene moiety are combined, typically in the presence of a coupling reagent (e.g., DCC). The result is an amide linkage formed between the amine group of the amine group-containing small molecule dantrolene moiety and the carbonyl of the carboxylic acid-bearing oligomer.

While it is believed that the full scope of the conjugates disclosed herein behave as described, an optimally sized oligomer can be identified as follows.

First, an oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A.H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by an NMR spectrometer manufactured by Bruker. A list of certain compounds as well as the source of the compounds is provided below.

Example 1

Synthesis of mPEGn-N-Dantrolene (n=3, 5 and 7)

mPEGn-N-Dantrolene was prepared. Schematically, the approach followed for this example is shown below.

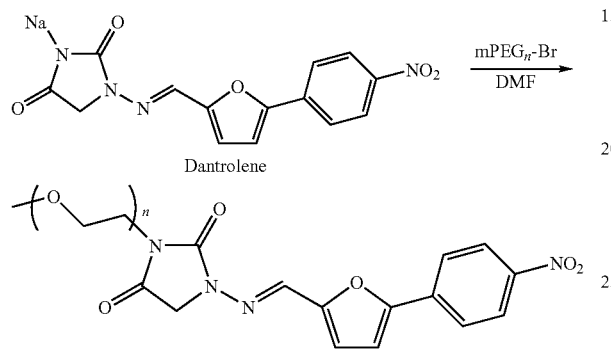

General synthesis of mPEGn-N-dantrolene (n=3, 5 and 7)

Dantrolene sodium salt (235 mg, 0.7 mmol) was dissolved in DMF (10 mL), and mPEGn-Br [n=3, 5, 7, in three separate runs] (0.8 mmol) was added to the solution. The resulting mixture was stirred under $N_2$ at 60° C. for 16 hours. Then the reaction mixture was cooled to room temperature and dichloromethane (200 mL) was added. The solution was washed with water (2×200 ml), and the organic phase was dried with sodium sulfate and the solvent removed under reduced pressure to give an orange solid. The solid was purified by column chromatography (Biotage flash chromatography system; A: MeOH, 1-4% (20 CV), 4-6% (10 CV), B: DCM). The product was obtained as orange solid (yield: ~90%). mPEG3-N-dantrolene (n=3 in the schematic above): [1]NMR (300 MHz, $CDCl_3$): δ 8.25 (d, 2H), 7.91 (s, 1H), 7.86 (d, 2H), 6.96 (s, 2H), 4.29 (s, 2H), 3.82 (m, 2H), 3.75 (m, 2H), 3.60 (m, 6H), 3.50(m, 2H), 3.34 (s, 3H). LC-MS: 461.1 (M+H$^+$). mPEG5-N-dantrolene (n=5 in the schematic above): $^1$H NMR (300 MHz, $CDCl_3$): δ 8.23 (d, 2H), 7.93 (s, 1H), 7.84 (d, 2H), 6.95 (s, 2H), 4.31 (s, 2H), 3.82 (m, 2H), 3.74 (m, 2H), 3.60 (m, 14H), 3.50(m, 2H), 3.34 (s, 3H).

LC-MS: 549.2 (M+H$^+$). mPEG7-N-dantrolene (n=7 in the schematic above): $^1$H NMR (300 MHz, $CDCl_3$): δ 8.25 (d, 2H), 7.91 (s, 1H), 7.86 (d, 2H), 6.96 (s, 2H), 4.29 (s, 2H), 3.82 (m, 2H), 3.75 (m, 2H), 3.60 (m, 22H), 3.50(m, 2H), 3.34 (s, 3H). LC-MS: 637.3.1 (M+H$^+$).

Example 2

Synthesis of mPEGn-O-Dantrolene (n=3, 5 and 7)

mPEGn-O-Dantrolene was prepared. Schematically, the approach followed for this example is shown below (unless otherwise stated, compound numbers in bold in the schematic correspond to the compound numbers provided in the text of this Example 2 alone).

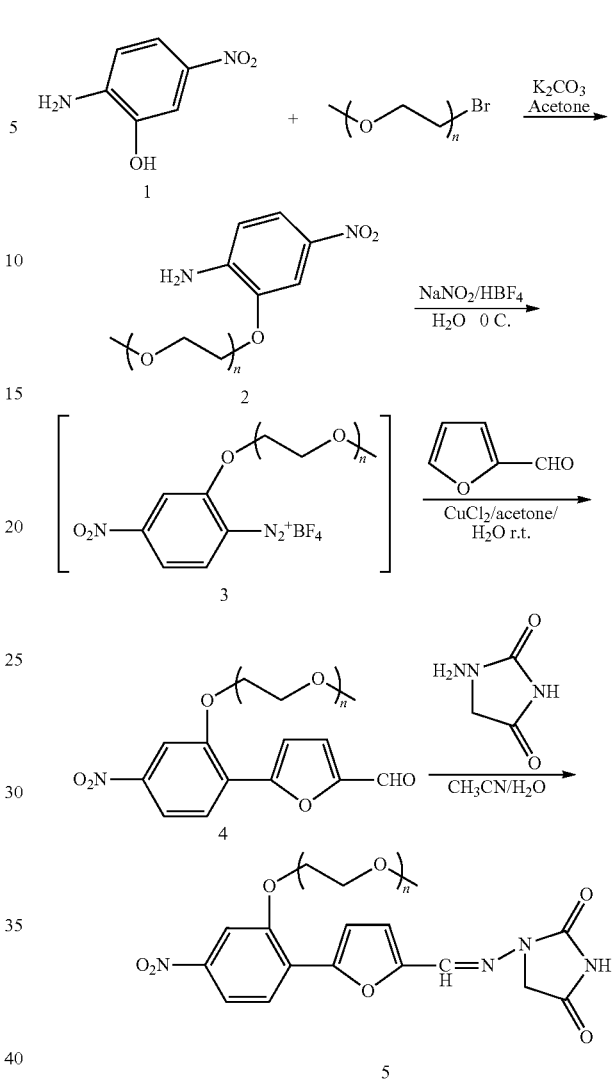

General Synthesis of mPEGn-O-dantrolene (n=3, 5 and 7)
Synthesis of compound (2)

2-Amino-5-nitrophenol (462 mg, 3.0 mmol) and mPEGn-Br [n=3, 5, 7, in three separate runs] (3.0 mmol) were dissolved in acetone (25 mL). $K_2CO_3$ (828 mg, 6.0 mmol) was added to the solution and the reaction was heated at reflux for four hours. The acetone was removed under reduced pressure and the residue was dissolved in DCM (300 mL). The organic phase was washed with $H_2O$ (2×300), dried over $Na_2SO_4$ and solvent was removed under reduced pressure. The product was used without further purification in the next reaction step. mPEG3-aminobenzonitrile (2a): $^1$H NMR (300 MHz, $CDCl_3$): δ 7.88 (d, 1H), 7.75 (s, 1H), 7.74 (d, 1H), 4.88 (br, 2H), 4.35 (m, 2H), 3.85 (m, 2H), 3.7 (m, 6H), 3.63(m, 2H), 3.40 (s, 3H). mPEG5-aminobenzonitrile (2b):
$^1$H NMR (300 MHz, $CDCl_3$): δ 7.88 (d, 1H), 7.75 (s, 1H), 7.74 (d, 1H), 5.05 (br, 2H), 4.35 (m, 2H), 3.85 (m, 2H), 3.75 (m, 2H), 3.7 (m, 12H), 3.63(m, 2H), 3.40 (s, 3H). mPEG7-aminobenzonitrile (2c): NMR (300 MHz, $CDCl_3$): δ 7.85 (d, 1H), 7.71 (s, 1H), 6.66 (d, 1H), 5.05 (br, 2H), 4.25 (m, 2H), 3.87 (m, 2H), 3.7-3.3 (m, 22H), 3.63(m, 2H), 3.38 (s, 3H).
Synthesis of Compound (4)
Compound (2) (1.0 mmol) [n=3, 5, 7, in three separate runs] was dissolved in water (3 mL), and 48% $HBF_4$ (0.6 g)

was added. The resulting solution was cooled in an ice-bath and then $NaNO_2$ (85 mg 1.2 mmol) was added dropwise. The mixture was stirred for 30 minutes at 0° C. A solution of 2-furaldehyde (384 mg, 4.0 mmol) in acetone (3 mL) was added followed by the addition of $CuCl_2$ (16 mg, 0.12 mmol) in water (0.5 mL). The reaction mixture was stirred at room temperature for 16 hours. Dichloromethane (200 mL) was added to the mixture and the organic phase was washed with $H_2O$ (200 ml×3), dried over $Na_2SO_4$ and the solvent removed under reduced pressure. The product was obtained as red sticky oil which was used in the next reaction step reaction without further purification.

Synthesis of mPEGn-O-dantrolene Conjugate (5)

Compound (4) [n=3, 5, 7, in three separate runs] was dissolved in $CH_3CN$ (10 mL), and then 1-aminohydantoin hydrochloride (450 mg, 3 mmol) in water (10 mL) was added. The solution was stirred at room temperature for one hour, and then DCM (200 mL) was added to the stirring solution. The organic phase was washed with $H_2O$ (200 ml×3), dried over $Na_2SO_4$, and the solvent removed under reduced pressure. The crude product was purified by column chromatography (Biotage flash chromatography system; A: MeOH, 1-4% (20 CV), 4-6% (10 CV), B: DCM). The product was obtained as yellow solid (overall yield: 40-60%). mPEG3-O-dantrolene (5a): $^1$H NMR (300 MHz, $CDCl_3$): δ 8.14 (d, 1H), 7.95 (s, 1H), 7.94 (d, 1H), 7.84 (s, 1H), 7.42 (d, 1H), 7.00 (d, 1H), 4.38 (m, 2H), 4.31 (s, 2H), 4.03 (m, 2H), 3.8 (m, 2H), 3.73(m, 2H), 3.68 (m, 2H), 3.55 (m, 2H), 3.38 (s, 3H). LC-MS: 477.2 (M+H$^+$). mPEG5-β-dantrolene (5b): $^1$H NMR (300 MHz, $CDCl_3$): δ 8.14 (d, 1H), 7.95 (d, 1H), 7.94 (s, 1H), 7.84 (s, 1H), 7.42 (d, 1H), 7.00 (d, 1H), 4.38 (m, 2H), 4.31 (s, 2H), 4.03 (m, 2H), 3.8 (m, 2H), 3.75(m, 12H), 3.68 (m, 2H), 3.38 (s, 3H). LC-MS: 565.2 (M+H$^+$). mPEG7-O-dantrolene (5c): $^1$H NMR (300 MHz, $CDCl_3$): δ 8.05 (d, 1H), 7.86 (d, 1H), 7.77 (s, 1H), 7.74 (s, 1H), 7.36 (d, 1H), 6.94 (d, 1H), 4.36 (m, 2H), 4.21 (s, 2H), 3.78 (m, 2H), 3.75 (m, 2H), 3.73 (m, 2H), 3.66 (m, 18H), 3.53 (m, 2H), 3.36 (s, 3H). LC-MS: 653.3 (M+H$^+$).

Example 3

Calcium Channel Binding Assay

The in vitro effects on calcium channels of dantrolene and the compounds prepared in Examples 1 and 2 were evaluated to determine their calcium channel blocking properties using the whole-cell patch clamp method in isolated human atrial myocytes.

Human myocytes were obtained from specimens of human right atrial appendage obtained during surgery from hearts of patients undergoing cardiopulmonary bypass. The isolation procedure produced rod-shaped, calcium tolerant cells which were used within 24 hours after isolation (Crumb et al., (1995) *Am J Physiol* 268:H1335-H1342).

The whole-cell patch clamp technique was carried out at 23±1° C. with precise micromanipulation under high power visual magnification to measure calcium currents. Glass pipettes were fire polished to produce tip diameters of 1-4 μm. The tip of the pipette, filled with electrolyte "internal" solution (a composition of (mM): 120 CsCl, 20 TEACl, 5 NaCl, 1 $CaCl_2$, 10 EGTA, 10 HEPES, 5 MgATP, 0.2 $Na_2GTP$, adjusted to pH 7.2 with CsOH) was positioned onto a cell. The cell was in a bathing "external" solution (consisting of (mM): 1.8 $CaCl_2$, 137 NaCl, 20 CsCl, 4 KCl, 1 $MgCl_2$, 10 HEPES, 10 dextrose, pH=7.4 with NaOH). Pipette tip resistance was approximately 1.0 to 2.0 MΩ when filled with the internal solution. Suction was then applied to the pipette interior to seal the cell membrane onto the tip. Another suction pulse then broke the membrane, establishing electrical access into the interior of the cell. The cellular interior then became dialysed by the solution the patch pipette was filled with.

After rupture of the cell membrane (entering whole-cell mode), current kinetics and amplitudes were allowed to stabilize (currents elicited by a series of voltage pulses given at 0.1 Hz were superimposed) as the cell was dialyzed with internal solution and paced at 1 Hz (3-5 minutes). Calcium current ($I_{Ca}$) was measured using a voltage pulse to 0 mV (200 ms duration) from a holding potential of −60 mV. Only a pacing rate of 0.1 Hz was used. Test article, at concentrations of 0.1, 1, 3, 10, 30, and 100 μM, was added in a cumulative manner to a cell.

Currents and voltages were recorded with patch-clamp amplifiers (Axopatch 1-B, Axon Instruments, Foster City, Calif.). Creation of voltage clamp pulses and data acquisition was controlled by a computer using electrophysiology software (pCLAMP version 9.2, Axon Instruments, Foster City, Calif.). Data was presented as % reduction of current amplitude, measured as current reduction after a steady-state effect had been reached in the presence of test article relative to current amplitude before introduction of test article (control). Each cell served as its own control.

All stock solutions (10 mM) were made by adding DMSO directly into the bottle containing the test article.

Figure 2:
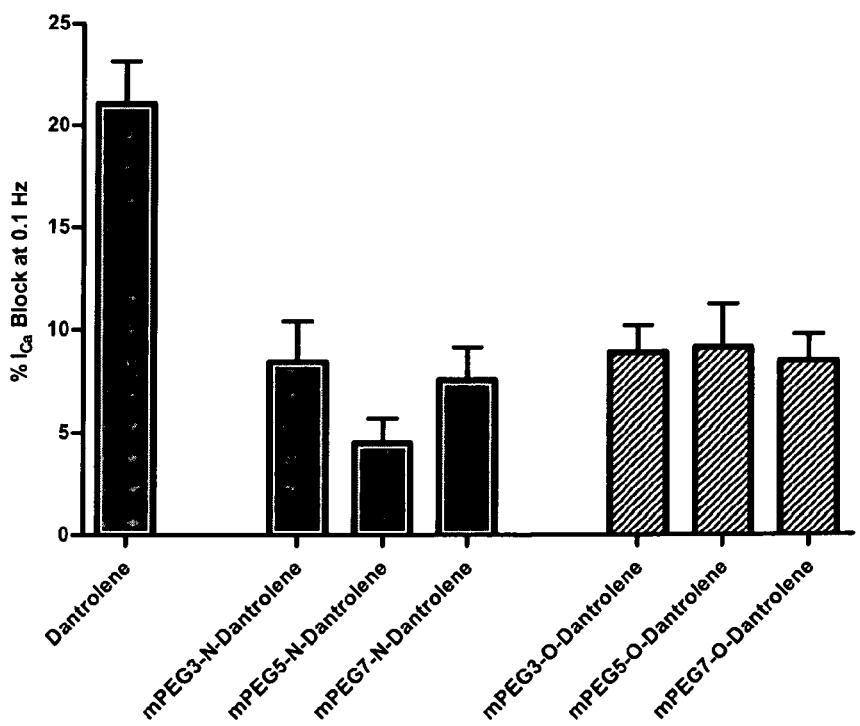
FIG. 2 is a bar graph showing the mean (with SEM) percent calcium current block at 0.1 Hz in isolated human atrial myocytes at 100 μM of dantrolene and the compounds prepared in Examples 1 and 2 as further explained in Example 3.

Dantrolene and the compounds prepared in Examples 1 and 2 were tested against the cardiac L-type calcium channel. All test articles were relatively weak blockers of $I_{Ca}$ amplitude (failing to reach an $IC_{50}$ value at 100 μM). Dantrolene exhibited the most block (21.1% at 100 μM); all compounds prepared in Examples 1 and 2 were less potent than the parent. Approximate $IC_{50}$ values (Table 1) were obtained from non-linear regression analysis of dose-response curves (FIG. 1) using GraphPad's Prism 5.01 software. Data was also analyzed for mean percent inhibition±SEM at the highest concentration tested, 100 μM (FIG. 2).

To test for cell sensitivity, 0.1 μM nisoldipine was added after exposure to test article. Exposure of 2 cells to nisoldipine resulted in a 100% reduction $I_{Ca}$ in both cells.

TABLE 1

Ca++ Channel Blocking Effects of Dantrolene and Compounds Prepared in Examples 1 and 2

| Compound | $IC_{50}$ at 0.1 Hz (M) | Fold Difference (Parent vs. Derivative) |
|---|---|---|
| Dantrolene | 1.04E−04 | 1 |
| mPEG3-N-Dantrolene | 1.11E−01 | 1067 |
| mPEG5-N-Dantrolene | 2.70E−02 | 260 |
| mPEG7-N-Dantrolene | 1.93E−04 | 2 |
| mPEG3-O-Dantrolene | 1.19E−01 | 1144 |
| mPEG5-O-Dantrolene | 5.43E−02 | 522 |
| mPEG7-O-Dantrolene | 4.62E−02 | 444 |

Example 4

LogP Data of the Compounds of Example 2

The LogP values of the compounds of Example 2 were determined using conventional techniques and employing a Sirius GLPKa instrument (Lakewood N.J.). The results are provided in Table 2.

TABLE 2

| LogP Data for Compounds Prepared in Example 2 | | |
| --- | --- | --- |
| Molecules | pKa | LogP |
| Dantrolene sodium salt | 7.11 | 1.89 |
| mPEG3-O-Dantrolene | 8.69 | −0.6 |
| mPEG5-O-Dantrolene | 7.49 | 0.74 |
| mPEG7-O-Dantrolene | 7.32 | 0.62 |

Example 5

Analgesic Assay

An analgesic assay was used to determine whether a given compound can reduce and/or prevent visceral pain in mice.

The assay utilized CD-1 male mice (5-8 mice per group), each mouse being approximately 0.015-0.030 kg on the study day. Mice were treated according to standard protocols.

Mice were given a single "pretreatment" dose of a compound lacking covalent attachment of a water-soluble, non-peptidic oligomer, a corresponding version comprising the compound covalently attached to a water-soluble, non-peptidic oligomer, or control solution (IV, SC, IP or orally) thirty minutes prior to the administration of the acetic acid solution. The animal was given an IP injection of an irritant (acetic acid) that induces "writhing" which may include: contractions of the abdomen, twisting and turning of the trunk, arching of the back and the extension of the hindlimbs. Mice were given a single IP injection (0.1 mL/10 g bodyweight) of a 0.5% acetic acid solution. After the injection the animals were returned to their observation enclosures and their behavior was observed. While the animals appeared "jumpy," the data is nonetheless instructive inasmuch as it was appeared to be possible to distinguish "writhing" from "jumpy" behavior. Contractions were counted between 0 and 20 minutes after the injection. The animals were used once. Each tested article was dosed at 1, 3 and 10 mg/kg (n=5 animals/dose).

Figure 3:
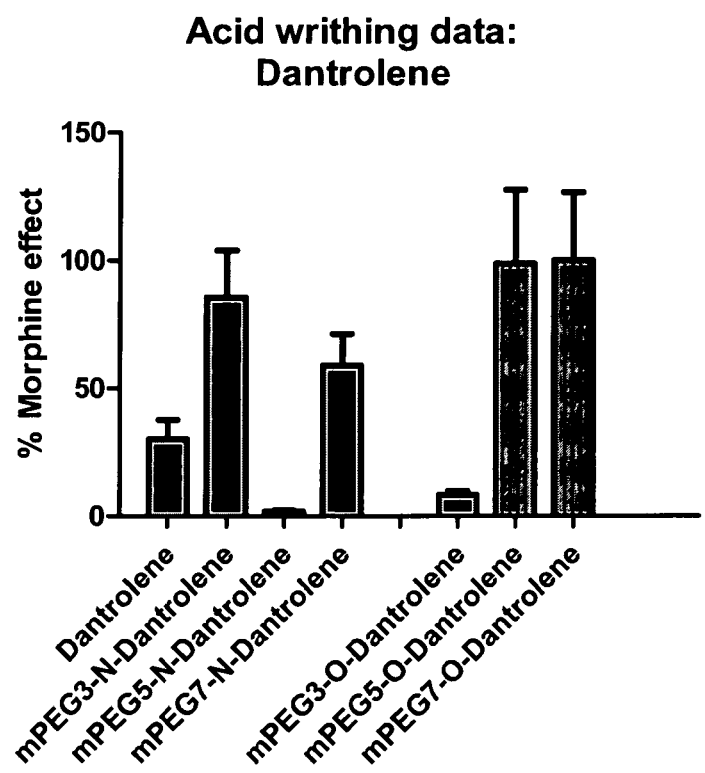
FIG. 3 is a graph of acid writhing data obtained as further explained in Example 5.

FIG. 3 shows the analgesia activity of the tested compound against the standard analgesic, morphine.

What is claimed is:

1. A compound having the following structure

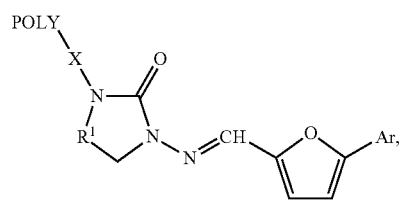

wherein:
R' is carbonyl;
Ar is phenyl optionally substituted with one or two substituents selected from the group consisting of nitro, cyano, amino, chloro, bromo, acetyl, carboxy, methyl and trifluoromethyl;
X is a spacer moiety; and
POLY is a water-soluble, non-peptidic oligomer having a molecular weight of below about 1500 Daltons.

2. The compound of claim 1, wherein the spacer moiety is a stable linkage.

3. The compound of claim 1, wherein the spacer moiety is a degradable linkage.

4. The compound of claim 1, wherein the spacer moiety is an ether linkage.

5. The compound of claim 1, wherein the spacer moiety is a direct covalent bond linkage.

6. The compound of claim 1, wherein the water-soluble, non-peptidic oligomer is a poly(alkylene oxide).

7. The compound of claim 6, wherein the poly(alkylene oxide) is a poly(ethylene oxide).

8. The compound of claim 1, wherein the water-soluble, non-peptidic oligomer has a number of repeating monomers in the range of from 1 to 50.

9. The compound of claim 1, wherein the water-soluble, non-peptidic oligomer has a number of repeating monomers in the range of from 1 to 30.

10. The compound of claim 9, wherein the poly(alkylene oxide) includes an alkoxy end-capping moiety.

11. A composition comprising a compound of claim 1, and (ii) optionally, a pharmaceutically acceptable excipient.

12. A composition of matter comprising a compound of claim 1, wherein the compound is present in a dosage form.

* * * * *

UNITED STATES PATENT AND TRADEMARK OFFICE
CERTIFICATE OF CORRECTION

PATENT NO. : 8,536,213 B2  
APPLICATION NO. : 12/742432  
DATED : September 17, 2013  
INVENTOR(S) : Riggs-Sauthier et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 500 days.

Signed and Sealed this  
Third Day of February, 2015

Michelle K. Lee  
*Deputy Director of the United States Patent and Trademark Office*